(12) United States Patent
Havelund

(10) Patent No.: US 6,211,144 B1
(45) Date of Patent: Apr. 3, 2001

(54) STABLE CONCENTRATED INSULIN PREPARATIONS FOR PULMONARY DELIVERY

(75) Inventor: Svend Havelund, Bagsværd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/419,668

(22) Filed: Oct. 15, 1999

Related U.S. Application Data

(60) Provisional application No. 60/105,986, filed on Oct. 28, 1998.

(51) Int. Cl.$^7$ .................................................. A61K 38/28
(52) U.S. Cl. .................................................. 514/4
(58) Field of Search .................................................. 514/4

(56) References Cited

U.S. PATENT DOCUMENTS

| | | | |
|---|---|---|---|
| 5,474,978 | | 12/1995 | Bakaysa et al. .......................... 514/4 |
| 5,506,203 | | 4/1996 | Backstrom et al. ...................... 514/4 |
| 5,743,250 | | 4/1998 | Gonda et al. ................... 128/200.14 |
| 5,747,445 | | 5/1998 | Backstrom et al. ...................... 514/4 |
| 5,783,556 | * | 7/1998 | Clark et al. .............................. 514/4 |
| 5,830,999 | * | 11/1998 | Dunn .................................... 530/303 |
| 5,866,538 | * | 2/1999 | Norup et al. ............................. 514/3 |
| 5,952,297 | * | 9/1999 | De Felippis et al. .................... 514/3 |
| 6,034,054 | * | 7/1998 | DeFelippis et al. ...................... 514/4 |

FOREIGN PATENT DOCUMENTS

| | | |
|---|---|---|
| 29 52 119 A1 | 7/1981 | (DE). |
| 0 692 489 A1 | 1/1996 | (EP). |
| WO 97/48413 | 12/1997 | (WO). |
| WO 98/42367 | 10/1998 | (WO). |
| WO 98/42368 | 10/1998 | (WO). |

OTHER PUBLICATIONS

Jens Brange, Stability of Insulin, Kluwer Academic Publishers (1992).
Brader et al., Biochemistry, vol. 30, pp. 6636–6645 (1991).
Galloway et al., Diabetes Care, vol. 4, pp. 366–376 (1981).
Bloom et al., J. Mol. Biol., vol. 245, pp. 324–330 (1995).
Derewenda et al., Nature, vol. 338, pp. 594–596 (1989).
Wollmer et al., Biol. Chem. Hoppe–Seyler, vol. 368, pp. 903–911 (1987).
Choi et al., Biochemistry, vol. 32 pp. 11638–11645 (1993).
Brzovic et al., Biochemistry, vol. 33, pp. 13057–13069 (1994).
Brems et al., Protein Engineering, vol. 5, pp. 519–525 (1992).
Elliott et al., Aust. Paediatr. J., vol. 23, pp. 293–297 (1987).
Okumura et al., International Journal of Pharmaceutics, vol. 88, pp. 63–72 (1992).
F. Sundby, The Journal of Biological Chemistry, vol. 237, pp. 3406–3411 (1962).
Robert F. Service, Science, vol. 277, pp. 1199–1200 (1997).
Dodson et al., Phil. Trans. R. Soc. Lond. A, vol. 345, pp. 153–164 (1993).
German abstract of article by Grau et al., Stabile Insulinosungen, pp. 411–419.
Kaarsholm et al., Archives of Biochemistry and Biophysics, vol. 283, pp. 496–502 (1990).

* cited by examiner

Primary Examiner—James H. Reamer
(74) Attorney, Agent, or Firm—Steve T. Zelson, Esq.; Reza Green, Esq.

(57) ABSTRACT

Concentrated aqueous insulin formulations of high physical and chemical stability are disclosed. The formulations are highly suitable for pulmonary delivery.

37 Claims, No Drawings

STABLE CONCENTRATED INSULIN PREPARATIONS FOR PULMONARY DELIVERY

CROSS-REFERENCE TO RELATED APPLICATIONS

This application claims priority under 35 U.S.C. 119 of Danish application PA 1998 01327 filed Oct. 16, 1998, and of U.S. Provisional application No. 60/105,986 filed Oct. 28, 1998, the contents of which are fully incorporated herein by reference.

FIELD OF THE INVENTION

The present invention relates to concentrated aqueous insulin formulations of high physical and chemical stability and being suitable for pulmonary delivery.

BACKGROUND OF THE INVENTION

Diabetes is a general term for disorders in man having excessive urine excretion as in diabetes mellitus and diabetes insipidus. Diabetes mellitus is a metabolic disorder in which the ability to utilize glucose is more or less completely lost. About 2% of all people suffer from diabetes.

Since the introduction of insulin in the 1920's, continuous strides have been made to improve the treatment of diabetes mellitus. To help avoid extreme glycaemia levels, diabetic patients often practice multiple injection therapy, whereby insulin is administered with each meal.

In solution, the self-association pattern of insulin is a complex function of protein concentration, metal ions, pH, ionic strength and solvent composition. For the currently used soluble preparations containing U100 insulin, zinc ions, isotonic agent and phenolic preservative, the following equilibria must be considered:

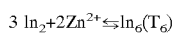

The known degradation patterns of insulin include a) fibril formation; b) deamidations at A18, A21 and B3; c) dimerisations via transamidation or Schiff-base formation; d) disulfide exchange reactions.

According to Brange (Stability of Insulin, Kluwer Academic Press,1994), each of these degradation reactions proceed much faster in the monomeric state than in the hexameric state. Therefore, the most efficient means of stabilising insulin preparations is by pushing the above equilibrium as far to the right as possible. In addition to this general effect of mass action, the reactivity of selected residues is further modified depending on their direct involvement in the T→R conformational change. Thus, the reactivity of B3Asn is much lower in the R-state (when the residue resides in an α-helix) than in the T-state.

The interconversion between $T_6$, $T_3R_3$ and $R_6$ conformations of the two zinc insulin hexamer is modulated by ligand binding to the $T_3R_3$ and $R_6$ forms. Anions such as chloride have affinity for the fourth coordination position in the metal ions of $T_3R_3$ and $R_6$, while preservatives such as phenol binds to hydrophobic pockets located near the surfaces of the $T_3R_3$ and $R_6$ forms (Derewenda, Nature 338, 594, 1989 and, Brzovic, Biochemistry 33, 130557, 1994). By the use of $Co^{2+}$ insulin it has been shown that the combined effect of anion and phenol binding is particularly efficient in stabilising the $R_6$ state. (Brader, Trends Biochem. Sci. 30, 6636, 1991 and; Bloom, J. Mol. Biol. 245, 324, 1995). Furthermore, for both $Zn^{2+}$- and $Co^{2+}$ insulin it has been shown that phenol is much more efficient than m-cresol in inducing R-state in the insulin hexamer (Wollmer, Biol. Chem. Hoppe-Seyler 368, 903, 1987 and, Choi, Biochemistry 32, 11638, 1993). High affinity phenol derivatives inducing R-state are 7-hydroxy-indol ((Dodson, Phil. Trans. R. Soc. Lond. A 345, 153, 1993) resorcinol and 2,6- and 2,7-dihydroxy-naphtalen ((Bloom, J. Mol. Biol. 245, 324, 1995).

The physical denaturation of insulin is known as fibrillation. In the fibrillar state extended peptide chains are laying parallel or anti parallel and hydrogen bonded to each other, so-called β-structure or β-pleated sheets. Fibrils represent usually the lowest state of energy of the protein, and only harsh conditions such as strong base may enable a regeneration from this state to the native state of correctly folded protein. Factors that promote the rate of formation of fibrils are increasing the temperature, increasing the surface area between the liquid and the air phase and, for zinc-free insulin, increasing the concentration. For hexameric zinc-insulin the rate of fibril formation decreases with increasing concentration. The formation of fibrils is believed to proceed via monomerization of insulin. Fibrils of insulin have the appearance of gels or precipitates.

Insulin derivatives having truncations in the C-terminal of the B-chain, e.g. des-pentapeptide (B26–B30) insulin and des-octapeptide (B23–B30) insulin are more prone to form fibrils than human insulin. Insulin analogues which dissociate readily from the hexameric unit to the monomeric form, e.g. the AspB28 human insulin and the LysB28–ProB29 human insulin, are likewise more prone to form fibrils than human insulin.

The native state of insulin is stabilised by bringing about the conditions that stabilises the hexameric unit, i.e. the presence of zinc ions (2–4 zinc/hexamer), phenol (0.1–0.5% w/v) and sodium chloride (5–150 mM).

Addition of agents that reduce the surface tension at the air-liquid interface further reduces the propensity to fibril formation. Thus, polyethylene glycol, polypropylene glycol and copolymers hereof with an average molecular weights of about 1800 have found use as stabilisers in concentrated insulin solutions for infusion pumps (Grau, 1982. In: Neue Insuline (Eds. Petersen, Schlüter & Kerp), Freiburger Graphische Betriebe, pp. 411–419 and Thurow,1981: patent DE2952119A1). For a comprehensive review on the physical stability of insulin see Brange 1994, Stability of Insulin, Kluwer Academic Publisher, pp. 18–23.

Most of the chemical degradation of insulin in preparations is due to reactions involving the carboxamide function of the asparagine residues, in particular residues B3 and A21. Hydrolysis of the amide groups leads to desamido derivatives, and transamidation involving an amino group from another molecule leads to covalently linked dimers and, after similar consecutive reactions, to trimers and higher polymers.

In acid solution AsnA21 is the most reactive, leading to AspA21 insulin (Sundby, J. Biol. Chem. 237, 3406, 1962). In crude insulin of bovine and porcine origin, obtained by acid ethanol extraction, the most abundant dimers isolated were AspA21 -GlyA1 and AspA21-PheB1 linked (Helbig 1976, Insulindimere aus der B-Komponente von Insulinpräparationen, Thesis at the Rheinisch-Westfälischen Technischen Hochschule, Aachen).

In neutral solution, which is the preferred embodiment of insulin preparations for injection therapy, AsnB3 is the most susceptible residue. Degradation products include AspB3 insulin, AspB3-GInB4 isopeptide insulin, and dimers and higher polymers where AspB3 provides the carbonyl moiety of a peptide bond with an amino group of another molecule. For a comprehensive review on the chemical stability of insulin see Brange 1994, Stability of Insulin, Kluwer Academic Publisher, pp. 23–36. As for the physical stability conditions that stabilises the hexameric unit, i.e. the presence of zinc ions (2–4 zinc/hexamer), phenol (0.1–0.5% w/v) and sodium chloride (5–150 mM), decrease the rate of formation of degradation products during storage at neutral pH.

A different type of polymerisation reaction is observed when the conditions that stabilises the hexameric unit is neglected. Thus, in the absence of zinc, phenol and sodium chloride, and using a temperature of 50° C., disulfide-linked dimers and high molecular weight polymers are the prevailing products formed. The mechanism of formation is a disulfide interchange reaction, resulting from β-elimination of the disulfides (Brems, Protein Engineering 5, 519, 1992).

Solubility of insulin is a function of pH, metal ion concentration, ion strength, phenolic substances, solvent composition (polyols, ethanol and other solvents), purity, and species (bovine, porcine, human, other analogues). For a review see Brange: Galenics of Insulin, Springer-Verlag 1987, p.18 and 46.

The solubility of insulin is low at pH values near its isoelectric pH, i.e. in the pH range 4.0–7.0. Highly concentrated solutions of porcine insulin (5000 U/ml~30 mM) have been brought about at acid pH (Galloway, Diabetes Care 4, 366, 1981), but the insulin in the formulation is highly instable due to deamidation at AsnA21. At neutral pH highly concentrated solutions of zinc free insulin can be made, but these are unstable due to a high rate of polymerisation and deamidation at AsnB3. Porcine zinc insulin solutions at neutral pH comprising phenol have been reported physical stable at concentrations of 1000 U/ml at elevated temperature, but become supersaturated when the temperature is lowered to 4° C. (Brange and Havelund in Artificial Systems for Insulin Delivery, Brunetti et al. eds, Raven Press 1983).

In order to reduce the inconvenience of insulin injections much attention has been given to alternative routes of administration (for an overview see Brange and Langkjaer in Protein Delivery: Physical Systems, Sanders and Hendren, eds., Plenum Press 1997). Pulmonary delivery seems to be the most promising of these (Service, Science 277, 1199. 1997). Insulin can be given aerolised in the form of dry powder or as nebulised droplets from an insulin solution. The efficacy might be enhanced by coached breathing (Gonda, U.S. Pat. No. 5,743,250) and addition of an absorption enhancer (Baekstroem, U.S. Pat. No. 5,747,445) or protease inhibitors (Okumura, Int. J. Pharm. 88, 63, 1992).

The bioavailability of a nebulised concentrated insulin solution (500 U/ml) was shown to be 20–25% as compared to a subcutaneous injection (Elliot, Aust. Paediatr. J. 23, 293, 1987). By using 30–50 µl insulin solution per puff the insulin solution need to be 5–20 times more concentrated than the usual concentration of 0.6 mM. By using a single dose container, e.g. a blister pack (Gonda, U.S. Pat. No. 5,743, 250), the demand for a preservative is abolished. Most insulin formulations are preserved by the toxic, mucose irritating and unpleasant odorous phenol and m-cresol. However, omitting phenols will cause stability problems. In addition to the bacteriostatic efficacy, the phenols act as physico-chemical stabilisers of insulin in combination with zinc ions. So, it is preferred that formulations of insulin for inhalation are made with a minimum concentration of phenol or that phenol has been replaced by more acceptable substitutes.

DESCRIPTION OF THE INVENTION

Definitions

By "analogue of human insulin" (and similar expressions) as used herein is meant human insulin in which one or more amino acids have been deleted and/or replaced by other amino acids, including non-codeable amino acids, or human insulin comprising additional amino acids, i.e. more than 51 amino acids.

By "derivative of human insulin" (and similar expressions) as used herein is meant human insulin or an analogue thereof in which at least one organic substituent is bound to one or more of the amino acids.

By "phenolic molecule" as used herein is meant phenol or any derivative thereof such as m-cresol or chloro-cresol.

Brief Description of the Invention

It is an object of the present invention to provide a concentrated insulin formulation for pulmonary delivery having an acceptable physical and chemical stability.

This object has unexpectedly been accomplished by providing an insulin formulation in which the concentration of chloride is kept below 50 mM, and in which the concentration of other anions such as phosphate is minimised.

Accordingly, the present invention relates to an aqueous insulin formulation comprising: 3 to 20 mM of human insulin or an analogue or a derivative thereof, less than 50 mM of chloride, less than 10 mM of any anions other than chloride and acetate, 2 to 5 $Zn^{2+}$ ions per six molecules of insulin, and at least 3 phenolic molecules per six molecules of insulin.

Preferred Embodiments

The insulin formulation according to the present invention preferably comprises 3 to 15, more preferably 4 to 15 mM, still more preferably 5 to 15 mM, even more preferably 6 to 15 mM of human insulin or an analogue or a derivative thereof.

In certain advantageous embodiments, the formulation of the invention comprises about 3 mM, about 6 mM, about 9 mM, about 12 mM, or about 15 mM of human insulin or an analogue or a derivative thereof.

When the insulin formulation of the invention is to be administered from multi-dose containers a preservative effect is desired and it may thus advantageously contain up to 50 mM of phenolic molecules. Surprisingly, however, adequate stability is obtained by using a relatively low concentration of phenolic molecules such as 3 to 12 phenolic molecules per six molecules of insulin, preferably 3 to 9 phenolic molecules per six molecules of insulin. A low concentration of phenolic molecules can be used when no or little preservative action is needed such as in single-dose containers. A further advantage of using a low amount of phenolic molecules is an increased convenience for the patient.

The insulin formulation according to the invention preferably contain less than 40 mM, more preferably less than 30 mM of chloride, still more preferably 5 to 20 mM of chloride, in order to secure optimal stability.

In a particular embodiment the insulin may comprise a low amount of phosphate buffer, preferably up to 5 mM of phosphate.

Insulin formulations of the invention comprising 2 to 4 $Zn^{2+}$ ions, preferably 2.2 to 3.2 $Zn^{2+}$ ions per six molecules of insulin, are very stable.

Insulin formulations of the invention comprising 3 to 5 $Zn^{2+}$ ions, preferably 3.5 to 5 $Zn^{2+}$ ions per six molecules of insulin, are also suitable.

Surprisingly, it is possible to add relatively high concentrations of zwitterions such as glycylglycine and glycine to the insulin formulation of the invention without decreasing the solubility of insulin. Glycylglycine acts as a buffer at neutral pH and furthermore increase the dissolution rate of zinc insulin at neutral to basic pH due to a moderately zinc chelating effect. Also, glycylglycine may act as a scavenger for amine reactions during the storage period. Thus, in a preferred embodiment the insulin formulation of the invention further comprises 5 to 150 mM of a zwitterionic amine, preferably glycylglycine or glycine.

In a preferred embodiment the insulin formulation of the invention further comprises 5 to 50 mM of trishydroxymethylaminomethan which acts as a buffer at neutral pH and as a scavenger for amine reactive compounds.

In another preferred embodiment the insulin formulation of the invention comprises sodium ions as cations. The sodium ion has a low salting out effect.

In another preferred embodiment the insulin formulation of the invention comprises potassium or a mixture of potassium and sodium ions as cations. Potassium ions in a concentration higher than the plasma concentration of 4–5 mM increase the transport of insulin through the lungs.

In another preferred embodiment potassium ion in a concentration more than 4–5 mM is used in combination with a mild bronchodilator such as menthol.

In another preferred embodiment the insulin formulation of the invention comprises between 0.001% by weight and 1% by weight of a non-ionic surfactant, preferably tween 20 or Polox 188. A nonionic detergent can be added to stabilise insulin against fibrillation during storage and nebulisation.

In another preferred embodiment the insulin formulation of the invention comprises 1 mM to 10 mM of an anionic surfactant, preferably sodium taurocholate, in order to further increase the bioavailabilty of insulin.

In a preferred embodiment the insulin used is human insulin.

In another preferred embodiment the insulin used is an analogue of human insulin wherein position B28 is Asp, Lys, Leu, Val or Ala and position B29 is Lys or Pro; or des (B28–B30), des(B27) or des(B30) human insulin.

The preferred analogues of human insulin are those in which position B28 is Asp or Lys, and position B29 is Lys or Pro, preferably $Asp^{B28}$ human insulin or $Lys^{B28}Pro^{B29}$ human insulin.

In another preferred embodiment the insulin is selected from the group of soluble long-acting insulin derivatives such as derivatives of human insulin having one or more lipophilic substituents, preferably acylated insulins.

The insulin derivative according to this embodiment is preferably selected from the group consisting of B29-$N^\epsilon$-myristoyl-des(B30) human insulin, B29-$N^\epsilon$-palmitoyl-des(B30) human insulin, B29-$N^\epsilon$-myristoyl human insulin, B29-$N^\epsilon$-palmitoyl human insulin, B28-$N^\epsilon$-myristoyl $Lys^{B28}Pro^{B29}$ human insulin, B28-$N^\epsilon$-palmitoyl $Lys^{B28}$ $Pro^{B29}$ human insulin, B30-$N^\epsilon$-myristoyl-$Thr^{B29}Lys^{B30}$ human insulin, B30-$N^\epsilon$-palmitoyl-$Thr^{B29}Lys^{B30}$ human insulin, B29-$N^\epsilon$-(N-palmitoyl-$\gamma$-glutamyl)-des(B30) human insulin, B29-$N^\epsilon$-(N-lithocholyl-$\gamma$-glutamyl)-des(B30) human insulin, B29-$N^\epsilon$-($\omega$-carboxyheptadecanoyl)-des(B30) human insulin and B29-$N^\epsilon$-($\omega$-carboxyheptadecanoyl) human insulin.

The most preferred insulin derivative is B29-$N^\epsilon$-myristoyl-des(B30) human insulin or B29-$N^\epsilon$-(N-lithocholyl-$\gamma$-glutamyl)-des(B30) human insulin.

The above soluble long acting insulin derivatives are albumin binding and have been designed to provide a constant basal supply of insulin (Markussen, Diabetologia 39, 281, 1996). Subcutaneous administration once or twice daily secures the required basal delivery of insulin, whereas for pulmonary administration several daily inhalations are recommended, preferably in connection with meals.

The insulin derivatives have a protracted onset of action and may thus compensate the very rapid increase in plasma insulin normally associated with pulmonary administration. By careful selection of the type of insulin, the present invention enables adjustment of the timing, and in order to obtain the desired insulin profile.

In a particular embodiment of the present invention, the insulin formulation comprises an insulin analogue or human insulin as well as an insulin derivative.

The phenolic molecules in the insulin formulation are preferably selected from the group consisting of phenol, m-cresol, chloro-cresol, thymol, or any mixture thereof.

The insulin preparation of the present invention preferably has a pH value in the range of 7 to 8.5, more preferably 7.4 to 7.9.

This invention is further illustrated by the following examples which, however, are not to be construed as limiting.

EXAMPLE 1

2.5 ml of a 21 mM insulin stock solution was made by dissolving 337 mg zinc free human insulin in 1237 $\mu$l water and adding 263 $\mu$l of 0.1 M $ZnCl_2$ and 637 $\mu$l water before adjusting pH with 38 $\mu$l of 0.2 M NaOH and finally adding water to 2.5 ml, calculating the specific volume of insulin as 0.7 $\mu$l/mg. A preparation of 15 mM was then made by adding 350 $\mu$l of 0.16 M m-cresol, 175 $\mu$l of 0.32 M phenol and salt or detergent to the concentrations shown in Table 1 and thereafter diluted by medium to 12, 9, 6, 3 and 0.6 mM and stored at 5° C.

EXAMPLE 2

Zinc insulin was dispersed in water (1:10) on icebath, added glycylglycine (7/15) equivalent and sodium hydroxide (3.1 equivalent) and stirred slowly overnight at 5° C. 0.1 equivalent of zinc chloride and detergent was then added, pH adjusted to 7.5 by 0.8 equivalent of hydrochloric acid and volume adjusted before adding phenol and water and finally diluting the 15 mM preparation with medium containing sodium chloride, glycylglycine and detergent to obtain 12, 9, 6, and 3 mM of human insulin. (Table 2 and 3).

The results are presented in the following Tables 1 to 3.

The data of Table 1 show that even a small amount of phosphate (e.g. 5 mM) reduce the stability of insulin, and substituting sodium chloride by trihydroxymethylaminomethan hydrochloride also tends to decrease the solubility of insulin. Contrary to salts the zwitterions glycylglycine and glycine increased the solubility of insulin, and it was possible to add unexpectedly high concentrations of the zwitterions glycylglycine and glycine without deteriorating the stabilising effect on insulin. Glycylglycine acts as a buffer at neutral pH and furthermore increases the dissolution rate of zinc insulin at neutral to basic pH due to a moderately zinc chelating effect. Glycylglycine may also act as a scavenger for amine reactions during storage. Addition of the non-ionic detergents tween 20 and poloxamer 188 up to 1% by weight and 3 mM of the anionic detergent sodium taurocholate did not reduce the stability at 5° C. storage.

An evaluation of the effect of a phenolic substance added equimolar to insulin is shown in table 2. Three of the phenolic molecules increase the physical stability from 6 to 15 mM of insulin or more at low temperature and reduce the formation of polymers at elevated temperature by a factor of 2–3 (at low chloride concentration). In another set of experiments (table 3) the relative amount of phenol or chlorocresol is varied from 0 to 2 per insulin at increasing chemical stability.

EXAMPLE 3

441 mg B29-N$^\epsilon$-(N-lithocholyl-$\gamma$-glutamyl)-des(B30) human insulin (143 nmol/mg) was suspended in 5 ml water at 0° C. and 220 μl 1 N NaOH added. After dissolution of the insulin analog 295 μl 0.1 M ZnCl$_2$ was added and the solution stirred until a temporary precipitate was dissolved. 315 μl 0.32 mM phenol and 98 μl 0.5 M glycylglycine and 70 μl 1% Tween 20 were subsequently added and pH measured to 7.60. Finally 693 μl water was added and the solution was passed through a sterile 0.22 μm Millex®-GV filter unit to obtain 7 ml 9 mM B29-N$^\epsilon$-(N-lithocholy-$\gamma$-glutamyl)-des(B30) human insulin. The solution remained stable after 3 months at 5° C.

TABLE 1

Stability of solutions of human insulin at conventional phenol/cresol concentrations (used for multiple dose containers) as a function of salt concentration, ion charge, and detergent concentration.

| Excipient 0.5 Zn$^{2+}$/insulin phenol and cresol 16 mM pH 7.5 and added (mM): | Physical stability of solution at 5° C. Maximal concentration without precipitation for 4 months. Test solutions were 0.6, 3, 6, 9, 12 and 15 mM insulin, respectively. |
|---|---|
| reference (norm. dissolution*) | 3–6 |
| reference (low ion strength) | 12 |
| NaCl 10 | 15 |
| NaCl 20 | 12 |
| NaCl 40 | 6 |
| NaCl 60 | <3 |
| NaH$_2$PO$_4$ 5 | |
| +NaCl 20 | 6 |
| +NaCl 25 | 6 |
| +NaCl 37.5 | 6 |
| +NaCl 50 | 6 |
| glycylglycine 7 | 15 |
| glycylglycine 12 | 15 |
| glycylglycine 24 | 15 |
| glycylglycine 48 | 15 |
| glycylglycine 72 | 15 |
| glycylglycine 96 | 15 |
| glycylglycine 120 | 15 |
| glycine 10 | 15 |
| glycine 20 | 15 |
| glycine 40 | 15 |
| glycine 60 | 15 |
| glycine 80 | 15 |
| glycine 100 | 15 |
| trishydroxymethylaminomethan**)7 | 12 |
| tris 12 | 9 |
| tris 24 | 9 |
| tris 48 | 3 |
| tween 20 0.05% | 15 |
| tween 20 0.2% | 15 |
| tween 20 1% | 15 |
| tween 20 5% | <3 |
| Polox 188 0.2% | 12 |
| Polox 188 1% | 12 |
| sodium taurocholate 3 | 12 |
| sodium taurocholate 15 | 9 |

*)addition of 1 μl 1N hydrochloric acid per mg insulin corresponding to about 6 equivalents of chloride.
**)neutralised by hydrochloric acid

TABLE 2

Stability of human insulin at equimolar concentrations of phenolic preservatives.

| Excipient 0.5 Zn$^{2+}$/insulin, NaCl 15 mM, glycylglycine 7 mM, tween 20 0.01%, pH 7.5 and equimolar; | Physical stability of solution at 5° C. Maximal stable concentration without precipitation for 3 months at 3, 6, 9, 12, 15 mM insulin | Chemical stability at 37° C. % polymer/week 3 and 15 mM insulin |
|---|---|---|
| cresol | 15 | 0.55  0.56 |
| phenol | 15 | 0.37  0.39 |
| chlor-cresol | 15 | 0.51  0.40 |
| thymol | 9 | 0.85  1.25 |
| reference (without phenolics) | 6 | 0.94  1.49 |

TABLE 3

Stability of human insulin at varied concentrations of phenolic preservatives.

| Excipient 0.5 Zn$^{2+}$/insulin, NaCl 15 mM, glycylglycine 7 mM, tween 20 0.01%, pH 7.5 and | Equivalent phenolic compound per insulin molecule | Chemical stability at 37° C. % polymer/week 3 and 9 mM insulin |
|---|---|---|
| reference | 0 | 0.99  1.43 |
| phenol | 0.33 | 0.69  0.96 |
| phenol | 0.67 | 0.52  0.55 |
| phenol | 1 | 0.46  0.38 |
| phenol | 2 and 1.33 | 0.27  0.26 |
| chloro-cresol | 0.33 | 0.66  0.93 |
| chloro-cresol | 0.67 | 0.48  0.58 |
| chloro-cresol | 1 | 0.30  0.30 |
| chloro-cresol | 2 and 1.33 | 0.13  0.18 |

What is claimed is:

1. An aqueous insulin formulation comprising: 3 to 20 mM of dissolved human insulin or an analogue or a derivative thereof, less than 50 mM of chloride, less than 10 mM of any anions other than chloride and acetate, 2 to 5 Zn$^{2+}$ ions per six molecules of insulin and at least 3 phenolic molecules per six molecules of insulin.

2. An insulin formulation according to claim 1 comprising 3 to 15 mM of human insulin or an analogue or a derivative thereof.

3. An insulin formulation according to claim 2 comprising 4 to 15 mM.

4. An insulin formulation according to claim 1 comprising up to 50 mM of phenolic molecules.

5. An insulin formulation according to claim 1 comprising less than 40 mM of chloride.

6. An insulin formulation according to claim 1 comprising up to 5 mM of phosphate.

7. An insulin formulation according to claim 1 comprising 2 to 4 Zn$^{2+}$ ions per six molecules of insulin.

8. An insulin formulation according to claim 1, further comprising 5 to 150 mM of a zwitterionic amine.

9. An insulin formulation according to claim 1, further comprising 5 to 50 mM of trishydroxymethylaminomethan.

10. An insulin formulation according to claim 1 comprising sodium ions, potassium ions, or a mixture thereof, as cations.

11. An insulin formulation according to claim 1, further comprising between 0.001% by weight and 1% by weight of a non-ionic surfactant.

12. An insulin formulation according to claim 1, further comprising 1 mM to 10 mM of an anionic surfactant.

13. An insulin formulation according to claim 1 comprising human insulin.

14. An insulin preparation according to claim 1, comprising an analogue of human insulin wherein position B28 is Asp, Lys, Leu, Val or Ala and position B29 is Lys or Pro; or des(B28–B30), des(B27) or des(B30) human insulin.

15. An insulin preparation according to claim 14, comprising an analogue of human insulin wherein position B28 is Asp or Lys, and position B29 is Lys or Pro, preferably $Asp^{B28}$ human insulin or $Lys^{B28}Pro^{B29}$ human insulin.

16. An insulin preparation according to claim 1, comprising a derivative of human insulin having one or more lipophilic substituents.

17. An insulin preparation according to claim 16, wherein the insulin derivative is selected from the group consisting of B29-$N^\epsilon$-myristoyl-des(B30) human insulin, B29-$N^\epsilon$-palmitoyl-des(B30) human insulin, B29-$N^\epsilon$-myristoyl human insulin, B29-$N^\epsilon$-palmitoyl human insulin, B28-$N^\epsilon$-myristoyl $Lys^{B28}$ $Pro^{B29}$ human insulin, B28-$N^\epsilon$-palmitoyl $Lys^{B28}$ $Pro^{B29}$ human insulin, B30-$N^\epsilon$-myristoyl-$Thr^{B29}Lys^{B30}$ human insulin, B30-$N^\epsilon$-palmitoyl-$Thr^{B29}Lys^{B30}$ human insulin, B29-$N^\epsilon$-(N-palmitoyl-$\gamma$-glutamyl)-des(B30) human insulin, B29-$N^\epsilon$-(N-lithocholyl-$\gamma$-glutamyl)-des(B30) human insulin, B29-$N^\epsilon$-($\omega$-carboxyheptadecanoyl)-des(B30) human insulin and B29-$N^\epsilon$-($\omega$-carboxyheptadecanoyl) human insulin.

18. An insulin preparation according to claim 17, wherein the insulin derivative is B29-$N^\epsilon$-myristoyl-des(B30) human insulin or B29-$N^\epsilon$-(N-lithocholyl-$\gamma$-glutamyl)-des(B30) human insulin.

19. An insulin preparation according to claim 1, comprising an insulin analogue or human insulin as well as an insulin derivative.

20. An insulin preparation according to claim 1, wherein the phenolic molecules are selected from the group consisting of phenol, m-cresol, chloro-cresol, thymol, and any mixture of any of the foregoing.

21. An insulin preparation according to claim 1 having a pH value in the range of 7 to 8.5.

22. A method of treating type I or type II diabetes, comprising administering to a patient in need of such treatment an insulin formulation according to claim 1.

23. A method according to claim 22, wherein insulin is administered in connection with meals.

24. An insulin formulation according to claim 3 comprising 5 to 15 mM of human insulin or an analogue or a derivative thereof.

25. An insulin formulation according to claim 24 comprising 6 to 15 mM of human insulin or an analogue or a derivative thereof.

26. An insulin formulation according to claim 1 comprising 9 mM of human insulin or an analogue or a derivative thereof.

27. An insulin formulation according to claim 2 comprising 12 mM of human insulin or an analogue or a derivative thereof.

28. An insulin formulation according to claim 1 comprising 3 to 12 phenolic molecules per six molecules of insulin.

29. An insulin formulation according to claim 28 comprising 3 to 9 phenolic molecules per six molecules of insulin.

30. An insulin formulation according to claim 5 comprising less than 30 mM of chloride.

31. An insulin formulation according to claim 30 comprising 5 to 20 mM of chloride.

32. An insulin formulation according to claim 7 comprising 7 comprising 2.2 to 3.2 $Zn^{2+}$ ions per six molecules of insulin.

33. An insulin formulation according to claim 8, wherein said zwitterionic amine is selected from the group consisting of glycylglycine and glycine.

34. An insulin formulation according to claim 11, wherein said non-ionic surfactant is selected from the group consisting of Tween-20™ (poly(oxyethylene)$_n$-sorbitan monolaurate) and Polox-188™ ($OH(CH_2CH_2O)_{75}(CH(CH_3)CH_2O)_{30}(CH_2CH_2O)_{75}H$).

35. An insulin formulation according to claim 12, wherein said anionic surfactant is sodium taurocholate.

36. An insulin formulation according to claim 1, wherein said insulin derivative is an acylated insulin derivative.

37. An insulin formulation according to claim 1, wherein said formulation has a pH between 7.4 and 7.9.

* * * * *